(12) United States Patent
Wei

(10) Patent No.: US 11,400,200 B2
(45) Date of Patent: Aug. 2, 2022

(54) DEVICE FOR AUTOMATICALLY COLLECTING SNOT

(71) Applicant: Shenzhen Dongjiang Technology Co., LTD, Shenzhen (CN)

(72) Inventor: Jun Jie Wei, Gongyi (CN)

(73) Assignee: Shenzhen Donjiang Technology Co., LTD, Shenzhen (CN)

( * ) Notice: Subject to any disclaimer, the term of this patent is extended or adjusted under 35 U.S.C. 154(b) by 0 days.

(21) Appl. No.: 17/585,614

(22) Filed: Jan. 27, 2022

(65) Prior Publication Data

US 2022/0143294 A1 May 12, 2022

(30) Foreign Application Priority Data

Dec. 24, 2021 (CN) .......................... 202123315107.X

(51) Int. Cl.
 *A61M 1/00* (2006.01)

(52) U.S. Cl.
 CPC ................ *A61M 1/65* (2021.05); *A61M 1/64* (2021.05); *A61M 1/76* (2021.05); *A61M 1/80* (2021.05); *A61M 2205/07* (2013.01); *A61M 2205/33* (2013.01); *A61M 2205/3584* (2013.01); *A61M 2205/587* (2013.01); *A61M 2205/8206* (2013.01); *A61M 2205/8256* (2013.01); *A61M 2210/0618* (2013.01)

(58) Field of Classification Search
 CPC .............. A61M 1/0003; A61M 1/0023; A61M 1/0058; A61M 1/0062; A61M 1/64; A61M 1/65; A61M 1/67; A61M 1/76; A61M 1/774; A61M 1/80; A61M 1/85; A61M 2205/07; A61M 2205/8206; A61M 2205/82; A61M 2210/0618; A61M 3/0208; A61M 3/0258; A61M 3/0283; A61M 1/784; A61B 2017/246; A61B 17/24; A61B 10/0045

See application file for complete search history.

(56) References Cited

U.S. PATENT DOCUMENTS

| | | | | | |
|---|---|---|---|---|---|
| 4,013,076 | A | * | 3/1977 | Puderbaugh | A61M 1/78 604/320 |
| 6,059,803 | A | * | 5/2000 | Spilman | A61M 1/0023 606/162 |
| 6,145,503 | A | * | 11/2000 | Smith | A61M 15/0021 128/202.16 |
| 6,589,219 | B1 | * | 7/2003 | Shibuya | A61M 1/78 604/319 |
| 6,595,949 | B1 | * | 7/2003 | Shapiro | A61M 1/0023 604/35 |

(Continued)

*Primary Examiner* — Adam Marcetich
(74) *Attorney, Agent, or Firm* — Wen IP LLC; Zhihua Han

(57) ABSTRACT

The present disclosure discloses a device for automatically collecting snot, which comprises a suction nozzle, a collecting cup, a cup holder and a shell component which are detachably connected in sequence, wherein the shell component is a hollow cavity. The present disclosure generates negative pressure suction through the air pump, and then the suction air enters the inner collecting cup through the air suction pipe, the cup holder air inlet, the air inlet channel and the micropore in sequence. Finally, the suction sucks the snot in the nose of a user into the inner collecting cup through the suction nozzle, effectively solving the problem of snot reflux.

14 Claims, 5 Drawing Sheets

(56) References Cited

U.S. PATENT DOCUMENTS

| | | | |
|---|---|---|---|
| 2002/0198488 A1* | 12/2002 | Yao | A61M 1/0062 |
| | | | 604/35 |
| 2003/0097142 A1* | 5/2003 | Wang | A61M 1/0023 |
| | | | 606/162 |
| 2005/0049620 A1* | 3/2005 | Chang | A61M 1/0058 |
| | | | 606/162 |
| 2008/0312674 A1* | 12/2008 | Chen | A61M 1/0058 |
| | | | 606/162 |
| 2009/0048581 A1* | 2/2009 | Sebban | A61M 1/0003 |
| | | | 604/319 |
| 2009/0076441 A1* | 3/2009 | Sebban | A61M 3/0208 |
| | | | 604/35 |
| 2009/0281482 A1* | 11/2009 | Baker | A61M 1/0058 |
| | | | 604/35 |
| 2009/0281485 A1* | 11/2009 | Baker | A61B 10/0045 |
| | | | 604/35 |
| 2010/0100075 A1* | 4/2010 | Weston | A61M 1/74 |
| | | | 604/543 |
| 2011/0144588 A1* | 6/2011 | Taylor | A61M 3/0208 |
| | | | 604/151 |
| 2012/0285268 A1 | 11/2012 | Maeda | |
| 2013/0174525 A1* | 7/2013 | Palmerton | A61M 1/0001 |
| | | | 55/355 |
| 2013/0178808 A1* | 7/2013 | Chen | A61M 1/78 |
| | | | 604/319 |
| 2014/0060716 A1 | 3/2014 | Windorfer | |
| 2017/0080132 A1* | 3/2017 | Huang | A61M 39/24 |
| 2017/0189769 A1 | 7/2017 | Chen | |
| 2017/0368273 A1* | 12/2017 | Rubin | A61M 16/0093 |
| 2018/0177936 A1* | 6/2018 | Ou Yang | A61M 1/0003 |
| 2019/0175202 A1* | 6/2019 | Piatyszek | A61M 1/80 |
| 2020/0306425 A1* | 10/2020 | Zhang | A61M 1/86 |

\* cited by examiner

DEVICE FOR AUTOMATICALLY COLLECTING SNOT

TECHNICAL FIELD

The present disclosure relates to the technical field of collecting devices, in particular to a device for automatically collecting snot.

BACKGROUND

Children catch a cold with nasal congestion, and they cannot suck out their snot. Nasal congestion will make them cry with poor breathing, which even affects sleep of children. A nasal aspirator can help parents take the secretions out of the nasal cavity for children to breathe smoothly. It is difficult for parents to use a traditional manual nasal aspirator, and it is not easy to suck out the secretions in the nasal cavity of children. Moreover, parents cannot grasp the strength of use, so that it is easy to hurt the nasal cavity of children. The existing nasal aspirator usually comprises a suction head and a main body part. The main body part is provided with an air pump, the suction head is provided with a cavity, and the opening of the cavity wall of the cavity forms a suction inlet. When the dirt is sucked into the cavity, it is easy to block the air suction inlet, and then the dirt is sucked into the main unit, such as the air pump, which is easy to cause damage to the main unit. Therefore, in view of the shortcomings of the above scheme in actual production, implementation and use, it is revised and improved. At the same time, with the help of professional knowledge and experience, this design is created with the spirit and idea of seeking excellence after many ingenious thoughts and experiments, so that a device for automatically collecting snot is provided to solve the above problems.

SUMMARY

One of the purposes of the present disclosure is to provide a device for automatically collecting snot to solve the above problems.

The device for automatically collecting snot of the present disclosure can be realized by the following technical scheme.

The present disclosure relate to a device for automatically collecting snot, comprising a suction nozzle, a collecting cup, a cup holder and a shell component which are detachably connected in sequence, wherein the shell component is a hollow cavity; a circuit board and an air pump fixed in the shell component; an air outlet pipe and an air suction pipe connected with the air pump in sequence, wherein one end of the air outlet pipe runs through the shell component; the cup holder is provided with a cup holder air inlet which is communicated with the air suction pipe; the collecting cup comprises an outer collecting cup and an inner collecting cup, the inner collecting cup is provided in the outer collecting cup, the inner collecting cup and the outer collecting cup are weld by ultrasonic waves, the inner collecting cup is provided with an air inlet channel, and the air inlet channel is communicated with the cup holder air inlet; a cup cover detachably connected to the collecting cup, which is an anti-reflux cup cover, wherein the cup cover is provided with a cup cover hole and at least one micropore, the cup cover hole is provided on the cup cover, and the at least one micropore is provided at the side of the cup cover hole; the suction nozzle is communicated with the inner collecting cup through the cup cover hole; the air suction pipe, the cup holder air inlet, the air inlet channel, the micropore and the suction nozzle form an air suction channel.

In one embodiment, the device for automatically collecting snot of the present disclosure further comprises a battery and a button, wherein the battery is fixedly provided in the shell component and is electrically connected with the circuit board, and the button is electrically connected with the circuit board and runs through the shell component.

In one embodiment, the battery is a rechargeable battery, which is a polymer lithium ion battery or 18650 battery.

In one embodiment, the device for automatically collecting snot of the present disclosure further comprises a charging interface which is electrically connected with the circuit board and runs through the shell component.

In one embodiment, the charging interface uses a Micro USB interface, a USB Type C interface or a Lightning interface.

In one embodiment, the button comprises a switch button and a function button.

In one embodiment, the device for automatically collecting snot of the present disclosure further comprises a speaker which is provided in the shell component and is electrically connected with the circuit board.

In one embodiment, the upper end of the shell component has a radian.

In one embodiment, the shell component comprises an upper shell, a lower shell and a cover plate; the upper shell and the lower shell are connected by a fastener structure or a screw structure, and the cover plate is provided on the upper shell.

In one embodiment, the cup holder is provided with a plurality of necks, the collecting cup is provided with a plurality of fasteners, and the plurality of fasteners are matched with the corresponding necks, respectively.

In one embodiment, the part in which the cup holder is in contact with the shell component, the part in which the cup holder is in contact with the collecting cup, and the part in which the collecting cup is in contact with the suction nozzle are all provided with sealing rings.

In one embodiment, the sealing ring is made of silica gel.

In one embodiment, the circuit board is further provided with a wireless communication module, and the wireless communication module is a 4G wireless module, a 5G wireless communication module, a WiFi wireless communication module or a Bluetooth wireless communication module.

In one embodiment, the outer collecting cup is made of transparent or semitransparent material, an LED lamp is provided in the cup holder and below the inner collecting cup, and the LED lamp is electrically connected with the circuit board.

In one embodiment, the inner collecting cup is provided with an air inlet channel, and the air inlet channel is oppositely positioned and assembled with the cup holder air inlet.

Compare with that prior art, the device for automatically collecting snot has the following beneficial effect.

In the device for automatically collecting snot of the present disclosure, the air pump works to generate negative pressure suction, and then the suction air enters the inner collecting cup through the air suction pipe, the cup holder air inlet, the air inlet channel and the micropore in sequence, and finally the suction sucks the snot in the nose of a user into the inner collecting cup through the suction nozzle. The air inlet channel is oppositely positioned and assembled with the cup holder air inlet. The flow direction of the air passage changes. In cooperation with the anti-reflux effect of the cup cover, the problem that the snot is sucked back into the shell component to damage the host can be effectively solved. At the same time, the micropores are provided on the cup cover. This design not only can ensure the normal air intake effect, but also further prevent the nose in the inner collecting cup from flowing backwards by using the negative pressure of the micropores.

BRIEF DESCRIPTION OF THE DRAWINGS

In order to explain the technical scheme of the embodiments of the present disclosure more clearly, the drawings needed in the embodiments will be briefly introduced hereinafter. It should be understood that the following drawings only show some embodiments of the present disclosure, so that they should not be regarded as limiting the scope. For those skilled in the art, other related drawings can be obtained according to these drawings without creative efforts.

Figure 1:
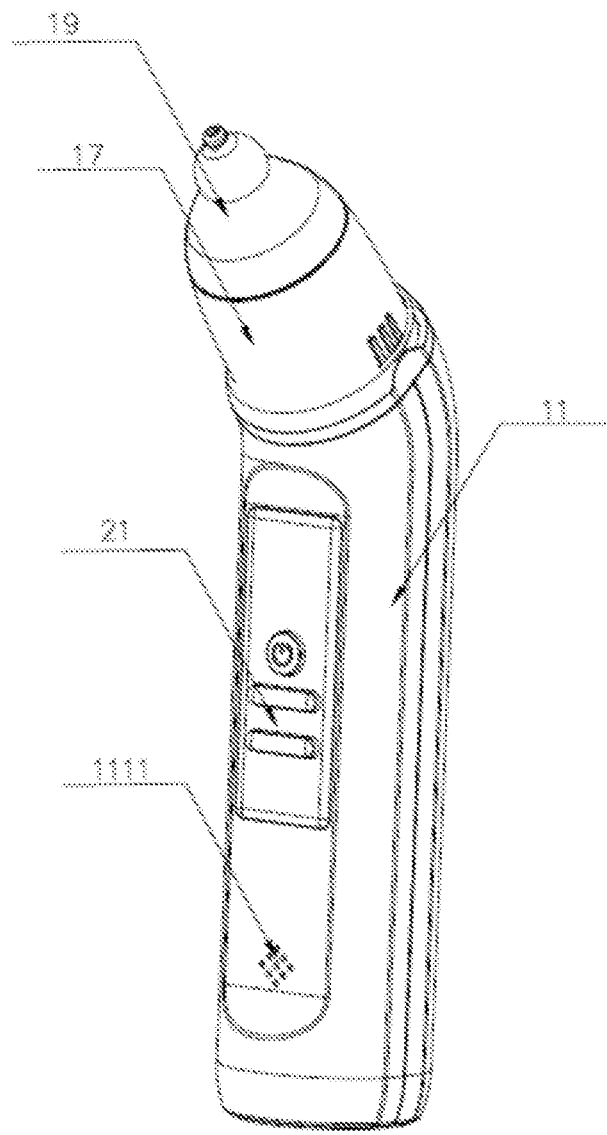
FIG. 1 is a schematic structural diagram of a device for automatically collecting snot according to the present disclosure.

Reference numbers in the drawing: 11. Shell component; 111. Upper shell; 1111. Speaker hole; 112. Lower shell; 113. Cover plate; 12. Circuit board; 13. Air pump; 14. Air outlet pipe; 141. Air outlet; 15. Air suction pipe; 16. Cup holder; 161. Cup holder air inlet; 162. Neck; 163. Sealing ring; 17. Collecting cup; 171. Outer collecting cups; 172. Inner collecting cups; 1721. Air inlet channel; 18. Cup cover; 181. Cup cover hole; 182. Micropore; 19. Suction nozzle; 191. Suction nozzle pipe; 20. Battery; 21. Button; 22. Display screen; 23. Charging interface; 24. Speaker; 25. LED lamp.

DETAILED DESCRIPTION OF THE EMBODIMENTS

In order to make the purpose, technical scheme and advantages of the embodiments of the present disclosure clearer, the technical scheme in the embodiments of the present disclosure will be clearly and completely described with reference to the drawings in the embodiments of the present disclosure hereinafter. Obviously, the described embodiments are part of the embodiments of the present disclosure, rather than all of the embodiments. Components of embodiments of the present disclosure generally described and shown in the drawings herein can be arranged and designed in various different configurations.

Therefore, the following detailed description of the embodiments of the present disclosure provided in the drawings is not intended to limit the scope of the claimed present disclosure, but only to represent selected embodiments of the present disclosure. Based on the embodiments in the present disclosure, all other embodiments obtained by those skilled in the art without creative efforts fall within the scope of protection of the present disclosure.

It should be noted that similar numbers and letters indicate similar items in the following drawings, so that once an item is defined in one drawing, it does not need to be further defined and explained in the following drawings.

In the description of the present disclosure, it should be noted that the orientation or positional relationship indicated by the terms "upper" and "lower" is based on the orientation or positional relationship shown in the drawings, or the orientation or positional relationship that the product of the present disclosure is usually placed when in use, which is only for the convenience of describing the present disclosure and simplifying the description, rather than indicating or implying that the indicated device or element must have a specific orientation, be constructed and operated in a specific orientation, so that it cannot be understood as a limitation of the present disclosure.

In addition, in the present disclosure, unless otherwise explicitly specified and limited, the first feature above or below the second feature may comprise the fact that the first feature is in direct contact with the second feature, or the first feature is not in direct contact with the second feature but is in contact through another feature between the first feature and the second feature. Furthermore, the first feature is above, on top of and on the second feature, which comprises the fact that the first feature is directly above and obliquely above the second feature, or simply indicates that the horizontal height of the first feature is higher than that of the second feature. The first feature is below, under and underneath the second feature, which comprises the fact that the first feature is directly below and obliquely below the second feature, or simply indicates that the horizontal height of the first feature is less than that of the second feature.

In addition, the terms such as "horizontal" and "vertical" do not mean that the components are required to be absolutely horizontal or vertical, but can be slightly inclined. For example, "horizontal" only means that its direction is more horizontal than "vertical", which does not mean that the structure must be completely horizontal, but can be slightly inclined.

In the description of the present disclosure, it should be noted that the terms such as "providing", "linking" and "connecting" should be understood broadly, for example, they can be fixed connection, detachable connection or integrated connection; they can be mechanical connection or electrical connection; they can be direct connection, or indirect connection through an intermediate medium, and the internal communication of two elements. For those skilled in the art, the specific meanings of the above terms in the present disclosure can be understood in specific situations.

As shown in FIGS. 1-5, a device for automatically collecting snot of the present disclosure mainly comprises a shell component 11, a circuit board 12, an air pump 13, an air outlet pipe 14, an air suction pipe 15, a cup holder 16, a collecting cup 17, a cup cover 18, a suction nozzle 19, a battery 20, a button 21, a display screen 22, a charging interface 23 and a speaker 24. The suction nozzle 19, the collecting cup 17, the cup holder 16 and the shell component 11 are detachably connected in sequence. The shell component 11 is a hollow cavity. The circuit board 12 and the air pump 13 are fixed in the shell component 11. The circuit board 12 is electrically connected with the air pump 13, the battery 20, the button 21, the display screen 22, the charging interface 23, the speaker 24 and the LED lamp 25, respectively. One end of the air outlet pipe 14 runs through the shell component 11, and the other end thereof is connected with the air pump 13. One end of the air suction pipe 15 is connected with the cup holder 16, and the other end thereof is connected with the air pump 13. The air pump 13 discharges air through the air outlet pipe 14 and sucks air through the air suction pipe 15. The cup holder 16 is provided on the shell component 11, in which a cup holder air inlet 161 is provided. The cup holder air inlet 161 is communicated with one end of the air suction pipe 15. The collecting cup 17 is detachably provided on the cup holder 16, in which an air inlet channel 1721 is provided. The air inlet channel 1721 is communicated with the cup holder air inlet 161. The collecting cup 17 is used to collect snot. The cup cover 18 is detachably connected to the collecting cup 17, which is an anti-reflux cup cover and is provided with a cup cover hole 181 and at least one micropore 182. The cup cover hole 181 is provided on the cup cover 18. The at least one micropore 182 is provided at the side of the cup cover hole 181. The suction air passing through the air inlet channel 1721 enters the collecting cup through the at least one micropore 182. The suction nozzle 19 is movably provided on the collecting cup 17, which runs through the cup cover 18 to be communicated with the collecting cup 17. The air suction pipe 15, the cup holder air inlet 161, the air inlet channel 1721, the micropore 182 and the suction nozzle 19 form an air suction channel. The battery 20 and the speaker 24 are fixedly provided in the shell component 11. The battery 20 provides electric energy for the circuit board 12. The speaker 24 provides sound prompt and alarm. The button 21, the display screen 22 and the charging interface 23 are electrically connected with the circuit board 12, respectively, and run through the shell component 11. The button 21 performs switching and function setting. The display screen 22 displays, and the charging interface 23 charges the battery 20.

Figure 3:
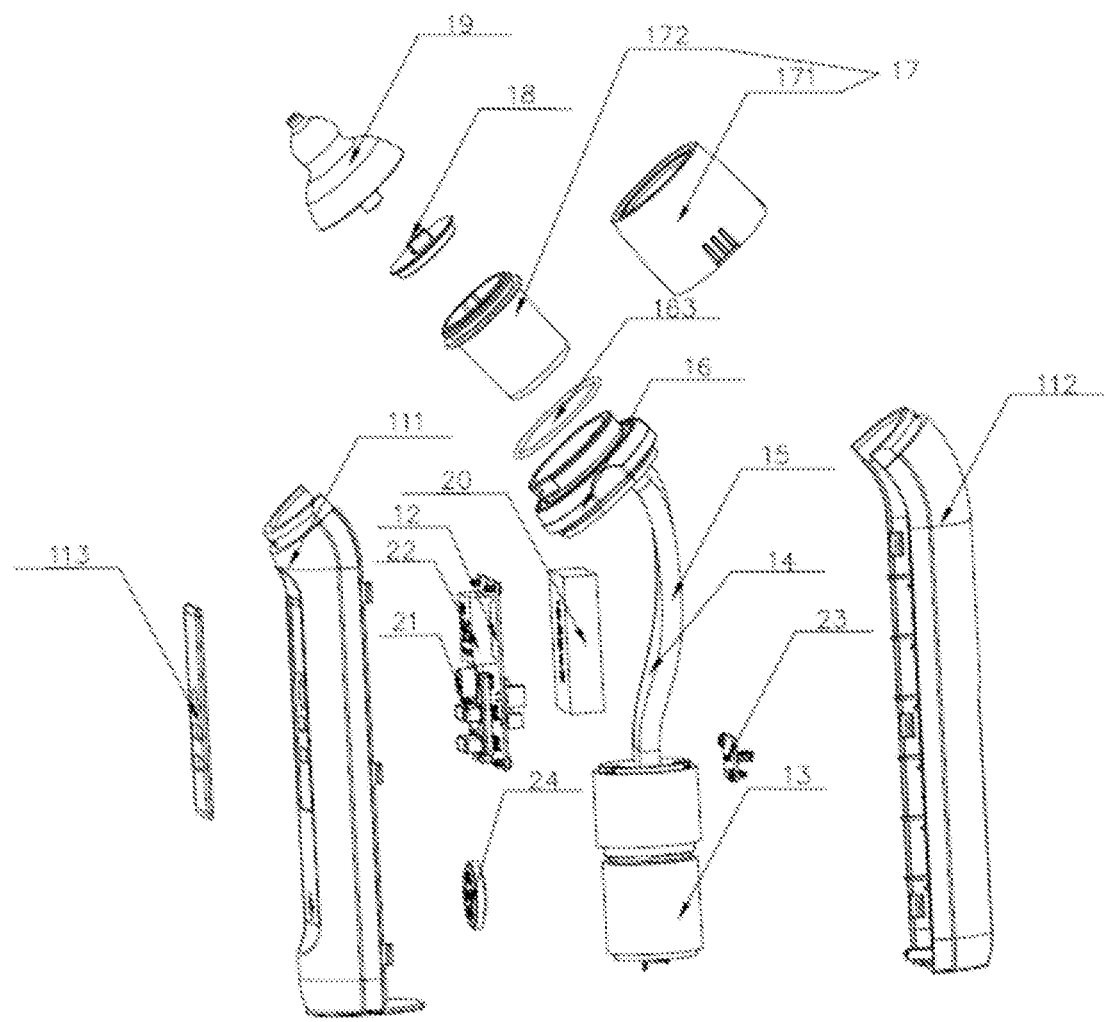
FIG. 3 is a schematic diagram of an explosion structure of a device for automatically collecting snot according to the present disclosure shown in FIG. 1.

As shown in FIG. 3, the upper end of the shell component 11 has a radian, which is convenient for putting the suction nozzle 19 into the nostril of the user. In this embodiment, the shell component 11 comprises an upper shell 111, a lower shell 112 and a cover plate 113. The upper shell 111 and the lower shell 112 are connected by a fastener structure or a screw structure, and they form a hollow cavity. The cover plate 113 is provided on the upper shell 111. In this embodiment, the upper shell 111 and the lower shell 112 are connected by a fastener structure. The cover plate 113 is a transparent panel, and the display of the display screen 22 can be observed through the cover plate 113. In this embodiment, the upper shell 111 is provided with a speaker hole 1111, and the position of the speaker hole 1111 corresponds to the position of the speaker 24.

Figure 4:
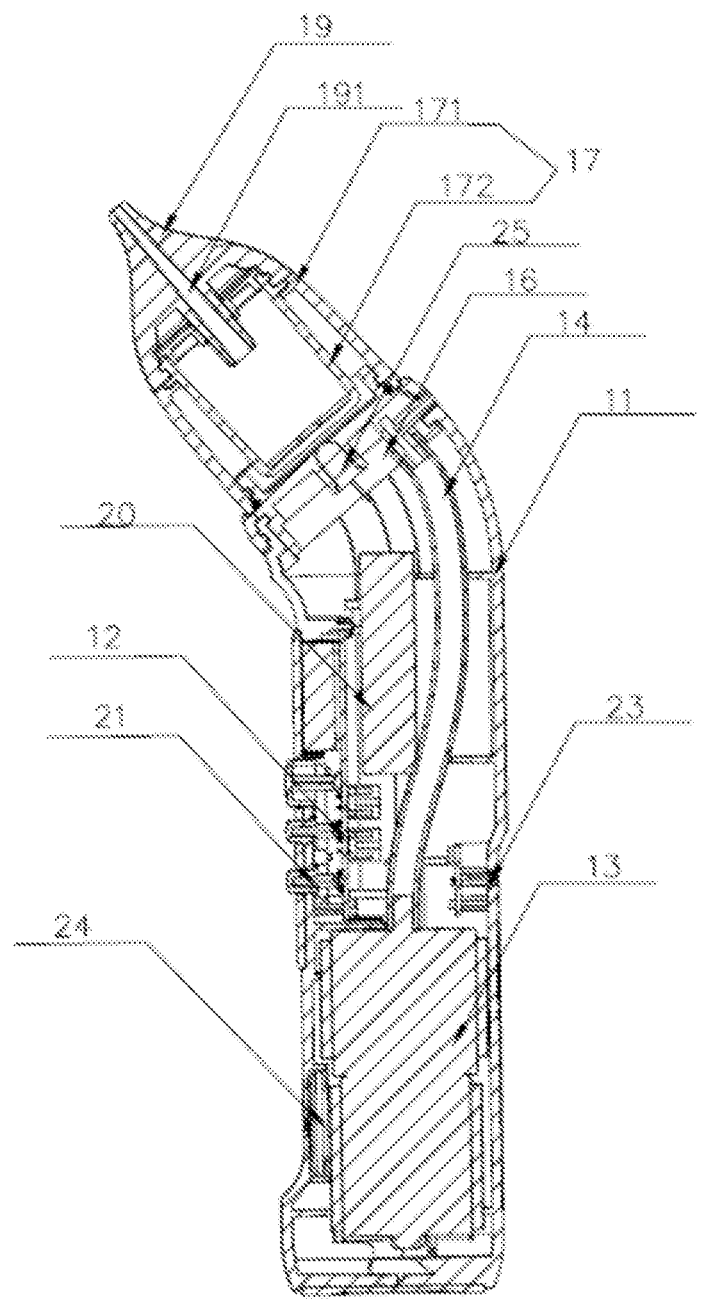
FIG. 4 is a schematic diagram of a cross-sectional structure of a device for automatically collecting snot according to the present disclosure shown in FIG. 1.

As shown in FIG. 3 and FIG. 4, in this embodiment, the circuit board 12 is electrically connected with the air pump 13, the battery 20, the button 21, the display screen 22, the charging interface 23, and the speaker 24, respectively. The control technology used by the circuit board is the existing technology, the specific structure and model of which will not be described in detail here. In other embodiments, the circuit board 12 is further provided with a wireless communication module, and the circuit board is wirelessly connected with external electronic terminals through the wireless communication module. The wireless communication module can be a 4G wireless module, a 5G wireless communication module, a WiFi wireless communication module or a Bluetooth wireless communication module.

Figure 2:
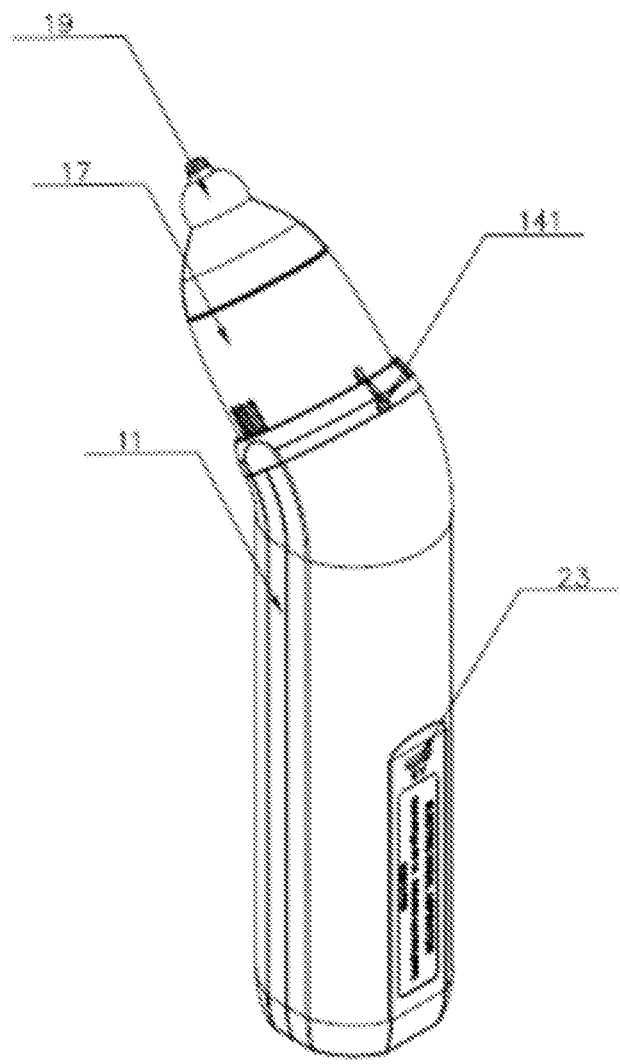
FIG. 2 is a schematic structural diagram of another side of a device for automatically collecting snot according to the present disclosure shown in FIG. 1.

As shown in FIG. 2, in this embodiment, the shell component 11 is provided with an air outlet 141 through which air is discharged.

Figure 5:
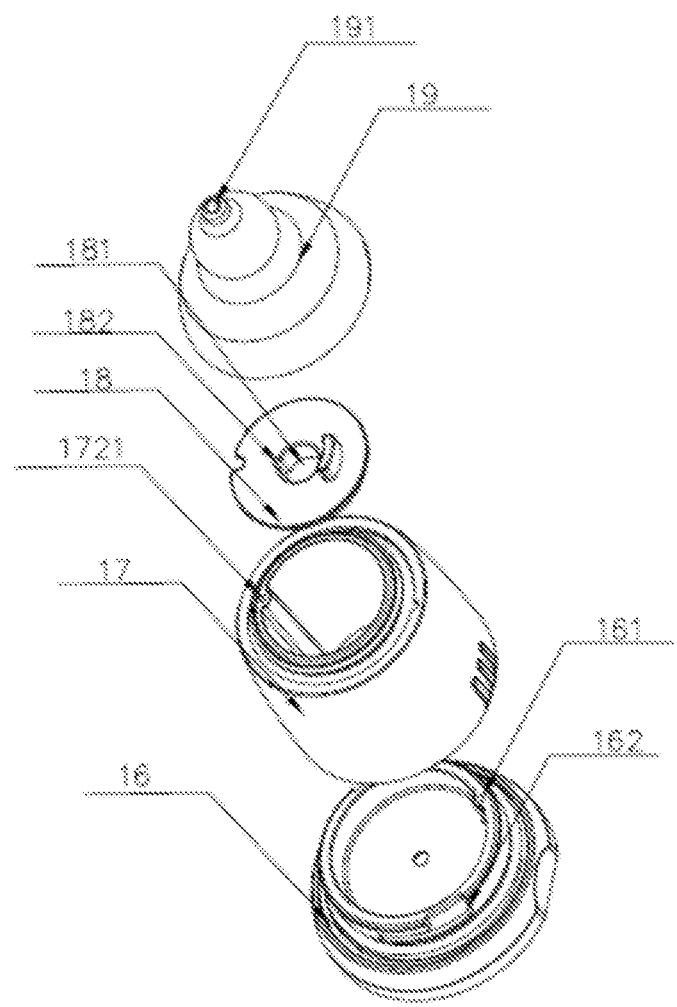
FIG. 5 is a schematic diagram of an explosion structure of an upper part of a device for automatically collecting snot according to the present disclosure shown in FIG. 1.

As shown in FIG. 5, the cup holder 16 is provided with a plurality of necks 162. The collecting cup 17 is provided with a plurality of fasteners. The plurality of fasteners are matched with the corresponding necks 162, respectively, so that the collecting cup 17 is installed on the cup holder 16. In this embodiment, in order to enhance airtightness, the part in which the cup holder 16 is in contact with the shell component 11, the part in which the cup holder 16 is in contact with the collecting cup 17, and the part in which the collecting cup 17 is in contact with the suction nozzle 19 are all provided with sealing rings 161. The sealing ring 161 is made of silica gel.

As shown in FIG. 3 and FIG. 4, in this embodiment, the collecting cup 17 comprises an outer collecting cup 171 and an inner collecting cup 172. The inner collecting cup 172 is provided in the outer collecting cup 171. The inner collecting cup and the outer collecting cup are weld by ultrasonic waves. In this embodiment, the inner collecting cup 172 is provided with an air inlet channel 1721. The air inlet channel 1721 is oppositely positioned and assembled with the cup holder air inlet 161. The flow direction of the air passage changes. In cooperation with the anti-reflux effect of the cup cover 18, the problem that the snot is sucked back into the shell component 11 can be effectively solved. The volume of the inner collecting cup 172 is 5-15 ml. In this embodiment, specifically, the volume of the inner collecting cup 172 is 10 ml. In this embodiment, the outer collecting cup 171 is made of transparent or semitransparent material. The LED lamp 25 is provided in the cup holder 16 and below the inner collecting cup 172. The LED lamp 25 is electrically connected with the circuit board 12. When the LED lamp 25 lights up, the light emitted by the LED lamp illuminates the inner collecting cup 172, so that the amount of snot in the inner collecting cup 172 can be seen through the outer collecting cup 171, thereby facilitating the user to clean the nose in the inner collecting cup 172 in time.

As shown in FIG. 3-FIG. 5, in this embodiment, the suction nozzle 19 is provided with a suction nozzle pipe 191. The suction nozzle pipe 191 extends into the collecting cup 17 through the cup cover hole 181. The suction nozzle pipe 191 is tightly connected with the cup cover hole 181. The suction air in the air inlet channel 1721 can only enter the inner collecting cup 172 through the at least one micropore 182. In this embodiment, the two micropores 182 are symmetrically provided at the side of the cup cover hole 181. This design not only can ensure the normal air intake effect, but also prevent the nose in the inner collecting cup 172 from flowing backwards by using the negative pressure of the two micropores 182.

As shown in FIG. 3 and FIG. 4, the battery 20 is a rechargeable battery. Specifically, the battery 20 is a polymer lithium ion battery or 18650 battery. In this embodiment, the battery 20 is a polymer lithium ion battery. In this embodiment, the button 21 comprises a switch button and a function button. The switch button is used to control the on/off of the device, and the function button is used to set the function. The display screen 22 can be an LED display screen or an LCD display screen. In this embodiment, the display screen 22 is an LED display screen. The charging interface 23 can be a Micro USB interface, a USB Type C interface or a Lightning interface. In this embodiment, the charging interface 23 uses a Micro USB interface.

It should be noted that the working process of the device for automatically collecting snot of the present disclosure is as follows: the air pump 13 works to generate negative pressure suction, and then the suction air enters the collecting cup 17 through the air suction pipe 15, the cup holder air inlet 161, the air inlet channel 1721, and the micropore 182 in sequence, and then the suction nozzle 19 sucks the snot in the nose of a user into the inner collecting cup 17.

The technical features of the above embodiments can be arbitrarily combined. For the sake of brevity, not all possible combinations of the technical features of the above embodiments are described. However, as long as there is no contradiction between the combinations of these technical features, they should be considered as the scope recorded in this specification.

The above embodiments only express several implementations of the present disclosure, which are described specifically in detail, but cannot be understood as limiting the patent scope of present disclosure. It should be pointed out that for those skilled in the art, several changes and improvements can be made without departing from the concept of the present disclosure, which fall within the scope of protection of the present disclosure. Therefore, the scope of protection of the patent of the present disclosure should be subject to the appended claims.

What is claimed is:

1. A device for automatically collecting mucus, comprising a suction nozzle, a collecting cup, a cup holder and a shell component which are detachably connected in sequence, wherein the shell component is a hollow cavity; a circuit board and an air pump fixed in the shell component; an air outlet pipe and an air suction pipe connected with the air pump in sequence, wherein one end of the air outlet pipe runs through the shell component; the cup holder is provided with a cup holder air inlet which is communicated with the air suction pipe; the collecting cup comprises an outer collecting cup and an inner collecting cup, the inner collecting cup is provided in the outer collecting cup, the inner collecting cup and the outer collecting cup are welded by ultrasonic waves, the inner collecting cup is provided with an air inlet channel, and the air inlet channel is communicated with the cup holder air inlet; a cup cover detachably connected to the collecting cup, wherein the cup cover is provided with a cup cover hole and at least one micropore filter, the cup cover hole is provided on the cup cover, and the at least one micropore filter is provided at a side of the cup cover hole; the suction nozzle is communicated with the inner collecting cup through the cup cover hole; the air suction pipe, the cup holder air inlet, the air inlet channel, the at least one micropore filter and the suction nozzle form an air suction channel.

2. The device for automatically collecting mucus according to claim 1, further comprising a battery and a button, wherein the battery is fixedly provided in the shell component and is electrically connected with the circuit board, and the button is electrically connected with the circuit board and runs through the shell component.

3. The device for automatically collecting mucus according to claim 2, wherein the battery is a rechargeable battery, which is a polymer lithium ion battery or 18650 battery.

4. The device for automatically collecting mucus according to claim 3, further comprising a charging interface which is electrically connected with the circuit board and runs through the shell component.

5. The device for automatically collecting mucus according to claim 4, wherein the charging interface uses a Micro USB interface, a USB Type C interface or a Lightning interface.

6. The device for automatically collecting mucus according to claim 2, wherein the button comprises a switch button and a function button.

7. The device for automatically collecting mucus according to claim 2, further comprising a speaker which is provided in the shell component and is electrically connected with the circuit board.

8. The device for automatically collecting mucus according to claim 1, wherein the upper end of the shell component has a curved section with a radius.

9. The device for automatically collecting mucus according to claim 8, wherein the shell component comprises an upper shell, a lower shell and a cover plate; the upper shell and the lower shell are connected by a fastener structure or a screw structure, and the cover plate is provided on the upper shell.

10. The device for automatically collecting mucus according to claim 1, wherein the cup holder is provided with a plurality of grooves, the collecting cup is provided with a plurality of fasteners, and the plurality of fasteners are matched with the corresponding grooves, respectively.

11. The device for automatically collecting mucus according to claim 1, wherein a joint between the cup holder and the shell component, a joint between the cup holder and the collecting cup, and a joint between the collecting cup and the suction nozzle are all provided with sealing rings.

12. The device for automatically collecting mucus according to claim 11, wherein the sealing ring is made of silicone.

13. The device for automatically collecting mucus according to claim 1, wherein the outer collecting cup is made of transparent or semitransparent material, an LED lamp is provided in the cup holder and below the inner collecting cup, and the LED lamp is electrically connected with the circuit board.

14. The device for automatically collecting mucus according to any of claims 1 to 13, wherein the inner collecting cup is provided with an air inlet channel, and the air inlet channel is oppositely positioned and assembled with the cup holder air inlet.

* * * * *